United States Patent [19]
Nanbu et al.

[11] Patent Number: 6,130,055
[45] Date of Patent: *Oct. 10, 2000

[54] METHOD FOR MEASURING THE CONCENTRATION OR THE ACTIVITY OF PROTEASE INHIBITOR

[75] Inventors: Atsuko Nanbu, Shiga; Satoshi Fukunaga, Osaka, both of Japan

[73] Assignee: Kyoto Daiichi Kagaku Co., Ltd., Kyoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/135,915

[22] Filed: Aug. 18, 1998

[30] Foreign Application Priority Data

Aug. 29, 1997 [JP] Japan ..................... 9-234850

[51] Int. Cl.⁷ ...................................... C12Q 1/34
[52] U.S. Cl. .............................. 435/18; 435/23; 435/184; 435/962
[58] Field of Search .............................. 435/18, 23, 69.2, 435/184, 962, 975

[56] References Cited

U.S. PATENT DOCUMENTS

| | | | |
|---|---|---|---|
| 5,354,491 | 10/1994 | Bjorkquist et al. | 252/135 |
| 5,777,081 | 7/1998 | Michalski et al. | 530/380 |
| 5,856,117 | 1/1999 | Uenoyama et al. | 435/23 |

FOREIGN PATENT DOCUMENTS

| | | |
|---|---|---|
| 0 168 738 | 1/1986 | European Pat. Off. . |
| 0 216 179 | 4/1987 | European Pat. Off. . |
| 7-155198 | 6/1995 | Japan . |
| 1160311 | 6/1985 | U.S.S.R. . |

OTHER PUBLICATIONS

Sigma Catalog, Sigma Chemical Co. p. 155, 1995.

1965, H.J. Faarvang, "Excretion of Mingin in Urine in Normal and in Pathological Conditions", *Scandinav. J. Clin. & Lab. Investigation 17* (Suppl. 83), pp. 25–28.

1974, "Measurement of Alpha₁–Antitrypsin in Serum, by immunodiffusion and by Enzymatic Assay", *Clinical Chemistry*, vol. 20, No. 3, pp. 396–399.

No Date Avail., Beatrice Kassell, "Bovine Trypsin–Kallikrein Inhibitor (Kunitz Inhibitor, Basic Pancreatic Trypsin Inhibitor, Polyvalent Inhibitor from Bovine Organs)", *Methods of Enzymatic Analysis*, 3rd Ed., vol. 10, pp. 844–845.

No Date Avail., Beatric Kassell, "Proteolytic Enzyme Inhibitors from *Ascaris lumbricoides*", *Methods of Enzymatic Analysis*, 3rd Ed., vol. 10, pp. 872–873.

May 1989, Shiro Kuwajima, et al., "Urinary trypsin inhibitor and its clinical usefulness for diagnosis of acute phase reactant and renal disease", *Japanese Journal of Inflammation* Review Article, vol. 9, No. 3, pp. 175–182 Abstract.

Apr. 1990, Shiro Kuwajima, et al., "Automated Measurement of Trypsin Inhibitor in Urine with a Centrifugal Analyzer: Comparison with Other Acute Phase Reactants", *Clinical Biochemistry*, vol. 23, pp. 167–171.

T. Bogacheva et al/. "Method for Determining the Molar Concentration of Protease Inhibitors and Their Enzyme Affinity", *Chemical Abtracts*, vol. 98, No. 5, p. 294 (Jan. 31, 1983). Abstract.

*Primary Examiner*—Ralph Gitomer
*Attorney, Agent, or Firm*—Merchant & Gould P.C.

[57] ABSTRACT

A method for measuring the concentration or the activity of UTI quickly and easily at high sensitivity. A urine sample, a buffer solution, a trypsin solution and a substrate solution are mixed and the trypsin activity is then measured. Thus, the UTI concentration in the urine sample is determined. In this case, a substrate solution having only L-BAPNA is used as the substrate, and the surfactant is mixed in at least one selected from the buffer solution and the enzyme solution. The mixing ratio of the surfactant is about 1 wt. % in the entire enzyme reaction solution. Examples of the surfactant include polyoxyethylene (40) octylphenylether, polyoxyethylene (10) octylphenylether, 3-[(3-cholamido propyl) dimethylammonio]-propanesulfonic acid, 3-[(3-cholamido propyl)dimethylammonio]-2-hydroxypropanesulfonic acid, and polyoxyethylene sorbitan monolaurate. As shown in FIG. 1, the sensitivity improves when using L-BAPNA.

8 Claims, 4 Drawing Sheets

FIG. 4(A)
FIG. 4(B)
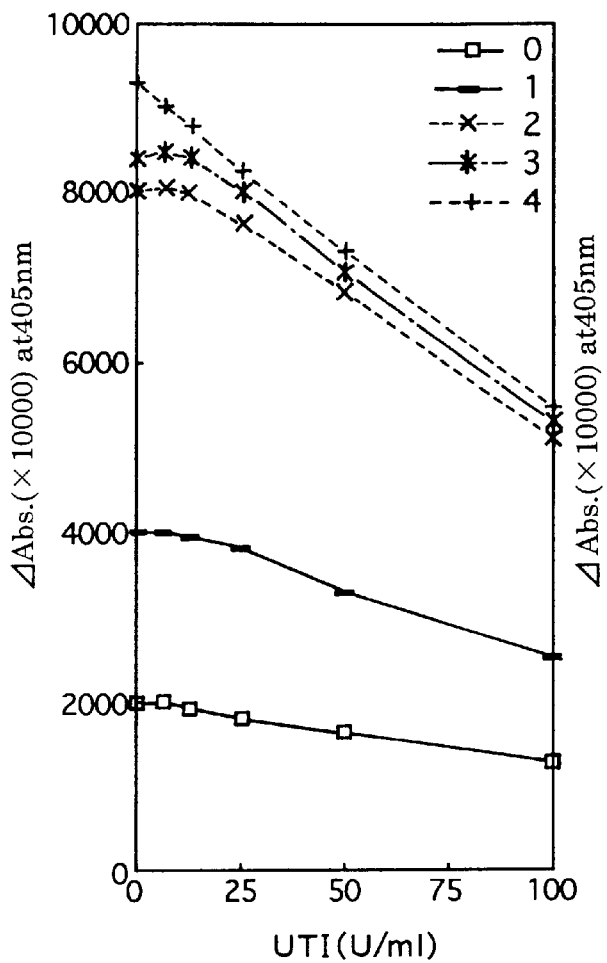
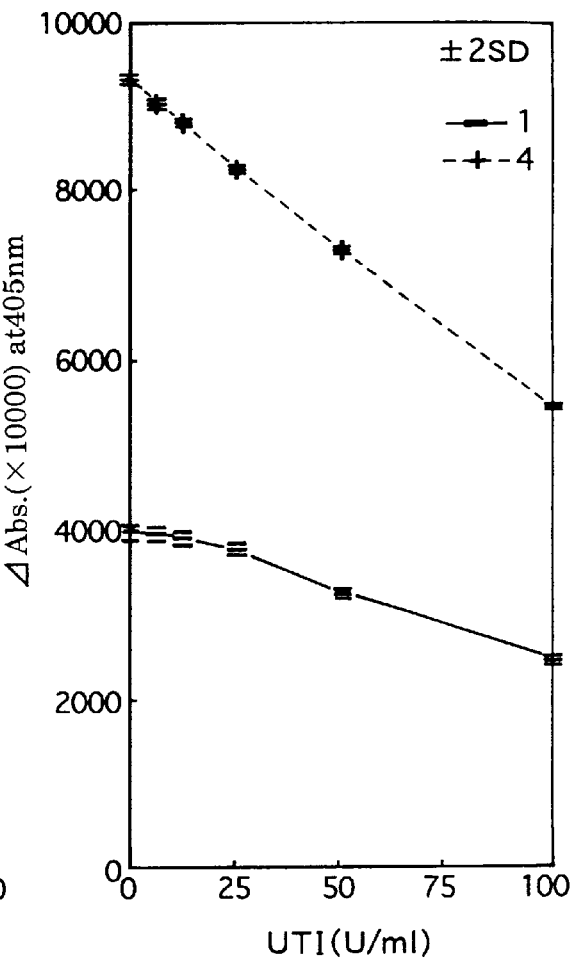
0 : 0.25g/L D,L-BAPNA
1 : 1g/L D,L-BAPNA, 2.5%-DMSO, 0.5%-CHAPSO
2 : 1g/L L-BAPNA, 2.5%-DMSO, 0.5%-CHAPSO
3 : 1g/L L-BAPNA
4 : 1g/L L-BAPNA, 0.25%-CHAPSO(R1 added)

METHOD FOR MEASURING THE CONCENTRATION OR THE ACTIVITY OF PROTEASE INHIBITOR

FIELD OF THE INVENTION

The present invention relates to a method for measuring the concentration or the activity of protease inhibitor and a measuring kit used in the same.

BACKGROUND OF THE INVENTION

Recently, urinary trypsin inhibitor (UTI) has been widely investigated as an indicator of organism conditions, and various examinations have been carried out in the field of clinical medicine. UTI is known, for example, to appear in urine when an organism is exposed to inner or outer stress, such as inflammation, surgery, or the like, or is infected ("Clinical Significance of Urinary Trypsin Inhibitor" by Shiro KUWAJIMA et al., JAPANESE JOURNAL OF INFLAMMATION REVIEW ARTICLE, VOL9, NO. 3, MAY 1989).

While such usefulness has been pointed out, UTI has not been fully applied in the field of clinical medicine and the like due to the insufficient sensitiveness in the conventional UTI measuring method.

In other words, since UTI inhibits trypsin activity corresponding to its amount, the concentration or the activity of UTI is measured by determining the inhibitory level of the trypsin activity. As an example of this method, there is a method for measuring the enzyme activity by mixing a urine sample with a buffer solution, then mixing the resultant solution with an enzyme (trypsin) solution, and adding a substrate solution therein. Generally, this measurement employs calcium as a trypsin activator. The calcium is usually mixed in the buffer solution.

In this measurement, benzoyl-arginine-p-nitroanilide (BAPNA) is widely used as a substrate. When trypsin cleaves this substrate, colors come out. The trypsin activity is determined by measuring the colors with a spectrophotometer. However, since this synthetic substrate has poor solubility, a substrate solution having a concentration of 1.0 g/L or more is difficult to prepare. Consequently, the enzyme activity depends on the substrate concentration, and therefore it has been difficult to improve the trypsin activity. On the other hand, an extremely small amount of UTI inhibits the trypsin activity. As described above, the concentration or the activity of UTI is measured by determining the inhibitory level of the trypsin activity. Therefore, when the trypsin activity cannot be determined at high sensitivity, the concentration or the activity of UTI also cannot be measured at high sensitivity.

In order to solve this problem, BAPNA is dissolved in a polar organic solvent, and the solvent is then diluted with water to double the volume, thus preparing a substrate solution. However, the use of such organic solvents makes it difficult to apply the measuring method mentioned above in an autoanalyser. In addition, the organic solvent might damage plastic cells used in general autoanalysis devices. Furthermore, the organic solvent might inhibit the protease activity such as trypsin and the like. Moreover, even if preparing the substrate solution by using an organic solvent, the substrate might be crystallized and precipitated in long-term storage or cold storage. Consequently, in the conventional measuring method, when dissolving the slightly soluble substrate such as BAPNA or the like by using an organic solvent mentioned above, it has been necessary to prepare the substrate solution for every measurement and carry out the measurement directly after the preparation. In addition, even if preparing the substrate solution using the organic solvent, the UTI sensitivity was not sufficient.

SUMMARY OF THE INVENTION

An object of the present invention is to provide a method for measuring the concentration or the activity of protease inhibitor easily and quickly at high sensitivity, with an aqueous solvent without using a polar organic solvent.

In order to attain the object mentioned above, the inventors developed the following first, second and third measuring methods.

The first measuring method is carried out by mixing a sample, protease, and a substrate in a solution and measuring the protease activity, thus determining the concentration or the activity of protease inhibitor in the sample. The first measuring method employs a substrate comprising one amino acid residue or more any of which is of L-type.

Generally, the synthetic substrate used in a protease-activity measurement is a compound of D-type and L-type amino acid residues. Compared to the compound substrate, the substrate having amino acid residues any of which is of L-type has excellent solubility, and a sufficient amount of the substrate can dissolve in water or hot water without using an organic solvent. The reason is not clear, but the inventors have confirmed the fact. For instance, even if using warm water, it is difficult to dissolve D, L-BAPNA at a concentration of 1 g/L or more. On the other hand, L-BAPNA can dissolve in warm water at a high concentration of 10 g/L. Furthermore, the use of the substrate having amino acid residues any of which is of L-type improves the protease activity. The reason also is not clear. However, the inventors surmise that the reason is not only the relative increase in the concentration of the L-type amino acid residues due to the elimination of the D-type amino acid residues that do not contribute to the enzyme reaction, but also the elimination of the enzyme inhibition by the D-type amino acid residues.

The second measuring method of the present invention is carried out by mixing a sample, protease, a substrate and a surfactant in a solution and measuring the enzyme activity of the protease, thus determining the concentration or the activity of protease inhibitor in the sample. In the second measuring method, the surfactant does not coexist with the substrate before being mixed in the solution.

In this measuring method, the use of the surfactant improves the protease activity, and therefore the inhibitor sensitivity improves. In this case, before preparing the enzyme reaction solution the surfactant must not coexist with the substrate by mixing with the substrate solution or the like. Therefore, it is necessary to mix the surfactant with a reagent other than the substrate solution such as a buffer solution, an enzyme solution or the like or with an enzyme reaction solution separately. It is not clear why the protease activity is improved by mixing the surfactant in such a manner, but the improvement is significant. In the second measuring method of the present invention, the substrate used is not particularly limited. Therefore, natural protein such as casein, peptide, a synthetic substrate in which D-type and L-type amino acid residues are mixed, or the like can be used.

In the present invention, an "enzyme reaction solution" means a solution that comprises enzyme and a substrate and causes an enzyme reaction. Therefore, even if a solution comprises both the enzyme and the substrate, the solution that does not cause the enzyme reaction due to the pH adjustment or the like is not an "enzyme reaction solution".

The third measuring method of the present invention is carried out by mixing a sample, protease, a substrate and a surfactant in a solution and measuring the enzyme activity of the protease, thus determining the concentration or the activity of protease inhibitor in the sample. The third measuring method employs a substrate solution comprising a substrate having one amino acid residue or more any of which is of L-type as mentioned above. The surfactant does not exist in the substrate solution before being mixed in the solution.

The third measuring method is a combination of the first measuring method and the second measuring method and has extremely high sensitivity.

In the measuring methods of the present invention, it is preferable that the surfactant concentration in the enzyme reaction solution is 0.01–2 wt. %, and more preferably 0.05–0.5 wt. %.

In the measuring methods of the present invention, it is preferable that the substrate is expressed by the following formula 1, wherein n is an integer of 1–5. As the substrate, α-benzoyl-L-arginine-p-nitroanilide is preferred.

Formula 1

Protecting Groups-(L-type Amino Acid Residues)$_n$-p-Nitroanilide

In the measuring methods of the present invention, the surfactant is preferably at least one selected from the group consisting of polyoxyethylene sorbitan monolaurate, polyoxyethylene sorbitan monooleate, polyoxyethylene sorbitan monostearate, sorbitan monopalmitate, sorbitan monooleate, sorbitan monolaurate, polyoxyethylene (10) octylphenylether, polyoxyethylene (30) octylphenylether, polyoxyethylene (40) octylphenylether, 1-O-n-octyl-β-D-glucopyranoside, sucrose monolaurate, 3-[(3-cholamido propyl)dimethylammonio]-propanesulfonic acid, 3-[(3-cholamido propyl)dimethylammonio]-2-hydroxypropanesulfonic acid, cetyltrimethylammonium bromide, and benzyltrimethylammonium hydroxide.

In the measuring methods of the present invention, it is preferable that the protease is trypsin, the sample is urine, the protease inhibitor is urinary trypsin inhibitor (UTI), and the enzyme activity is measured in the presence of calcium.

Corresponding to the three types of the measuring methods described above of the present invention, there are the following three types of measuring kits, a first, a second and a third measuring kits, for measuring the concentration or the activity of protease inhibitor in the present invention.

The first measuring kit comprises protease and a substrate and is used for measuring the concentration or the activity of protease inhibitor. The substrate solution comprises the substrate having one amino acid residue or more any of which is of L-type.

The second measuring kit comprises protease, a substrate and a surfactant and is used for measuring the concentration or the activity of protease inhibitor. Before mixing the three reagents described above, the surfactant and the substrate do not coexist.

The third measuring kit comprises protease, a substrate and a surfactant and is used for measuring the concentration or the activity of protease inhibitor. The substrate solution comprises the substrate having one amino acid residue or more any of which is of L-type, and the surfactant does not exist in the substrate solution.

The use of such measuring kits of the present invention enables the concentration or the activity of protease inhibitor to be measured quickly and easily at high sensitivity.

It is preferable that the measuring kits of the present invention comprise a buffer solution (R1), a protease solution (R2), a substrate solution (R3) and at least one selected from the buffer solution (R1) and the protease solution (R2) comprises a surfactant.

In these measuring kits, the R1, R2 and R3 mentioned above may be provided independently or in the combination of a mixture of any two solutions selected from the three solutions and the other one solution. Specifically, there are the following three combinations.

(1) A mixture of R1 and R2+R3
(2) A mixture of R1 and R3+R2
(3) A mixture of R2 and R3+R1

In the combination (3) described above, when controlling the enzyme reaction, for instance, by adjusting its pH, the enzyme and the substrate can be mixed.

In the measuring kits of the present invention, it is preferable that the surfactant concentration is adjusted in the range of 0.01–2 wt. % in the enzyme reaction solution, more preferably 0.05–0.5 wt. %.

The preferable substrate and surfactant used in the measuring kits of the present invention are the same as those described above in the measuring method of the present invention.

It is preferable that in the measuring kits of the present invention, calcium is also included, the measuring sample is urine, the protease is trypsin, and the protease inhibitor is urinary trypsin inhibitor (UTI). These kits enable the concentration or the activity of the UTI to be measured quickly and easily at high sensitivity.

BRIEF DESCRIPTION OF THE DRAWINGS

FIG. 4 (A) and (B) are two graphs showing the results of the UTI measurement using substrate solutions prepared by employing 5 formulations in one example of the measuring method of the present invention.

DETAILED DESCRIPTION OF THE INVENTION

Embodiment

Figure 1:
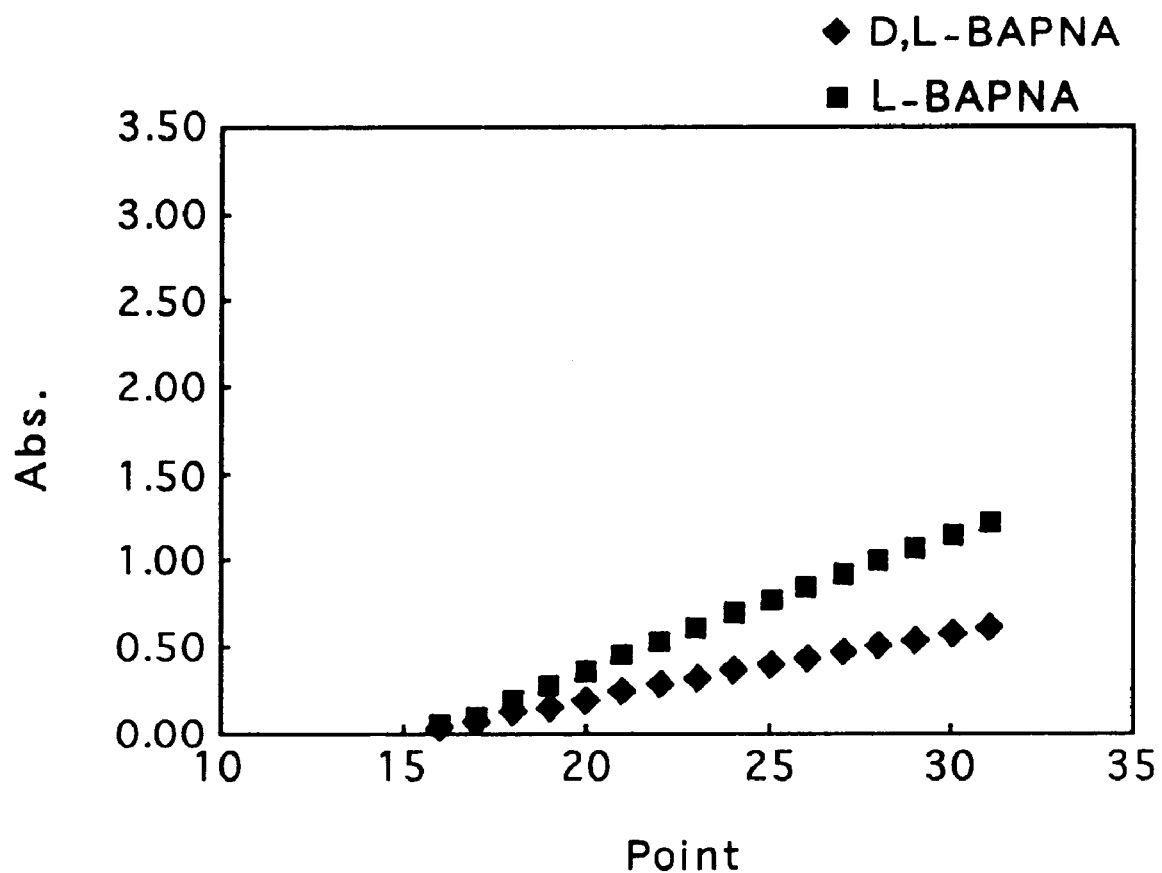
FIG. 1 is a graph showing the results of the sensitivity comparison using L-BAPNA and D, L-BAPNA in an example of the measuring method of the present invention.

The present invention will be explained below in detail.

The method for measuring the concentration or the activity of protease inhibitor of the present invention is carried out by using, for example, a protease solution, a substrate solution comprising the substrate having one amino acid residue or more any of which is of L-type, and a buffer solution.

An example of the protease described above is trypsin. The trypsin is not specifically limited and there are, for example, bovine pancreas trypsin and porcine pancreas trypsin. The specific activity of the trypsin or the like determines the trypsin concentration suitably. However, the concentration is usually 1–500 mg/L, preferably 10–100 mg/L in the entire enzyme solution. This enzyme solution may be adjusted to a pH of 2.0–3.5 by using hydrochloric acid or a buffer solution for the purpose of preventing autolysis of the trypsin.

Besides trypsin, chymotrypsin is another example of the protease. The substrate used in the chymotrypsin is, for example, benzoyl-L-tyrosine-p-nitroanilide.

The substrate solution comprises the substrate having one amino acid residue or more any of which is of L-type. Beside the substrate described above, the preferred substrates include, for example, Z-glycine-glycine-L-leucine-p-nitroanilide, and succinyl-L-alanine-L-alanine-L-alanine-p-nitroanilide. Such are substrates having amino acid residues any of which is of L-type generally available in the market (for instance, one marketed by Sigma Chemical Co.) or can be also obtained by dividing the compound comprising D-type and L-type amino acid residues by optically active chromatography or the like. The substrate concentration is generally in the range of 1–10 g/L. The solvent used for preparing the substrate solution is usually water (purified water or the like), but may be the buffer solution described below. The substrate solution can be prepared by, for example, warming the solvent such as water and adding substrate therein.

The buffer solution described above is not specifically limited, and examples are triethanolamine hydrochloride buffer solution, tris hydrochloric acid buffer solution, phosphate buffer solution, Good's buffer solution or the like. The buffer solution is prepared by the usual methods. The optimum pH of the enzyme in which this buffer solution is used determines the pH of the buffer solution. For example, when using the buffer solution in trypsin, the pH is preferably 7–8. When measuring the concentration or the activity of trypsin inhibitor, calcium is generally mixed in a buffer solution, and its ratio is usually 0.01–0.5 wt. %.

One of the characteristics of the present invention is to use a surfactant. The surfactant has no limitation in kind. Any ionic surfactant, ampholytic surfactant or nonionic surfactant may be used. The optimum range of the amount to be used is also determined suitably depending on the kind of surfactant.

Cetyltrimethylammonium bromide and benzyltrimethylammonium hydroxide are examples of the ionic surfactant described above. The amount to be used is usually 0.01–2 wt. %.

Examples of the nonionic surfactant described above include polyoxyethylene(40) octylphenylether (for instance, TRITON X-405, manufactured by Nacalai Tesque, Inc.), polyoxyethylene(10) octylphenylether (for instance, TRITON X-100, manufactured by Nacalai Tesque, Inc.), polyoxyethylene sorbitan monolaurate (for instance, Tween 20, manufactured by Nacalai Tesque, Inc.), and polyoxyethylene sorbitan monooleate (for instance, Tween 80, manufactured by Nacalai Tesque, Inc.). The amount to be used is usually 0.01–2 wt. %.

Examples of the ampholytic surfactant described above include, for example, 3-[(3-cholamido propyl) dimethylammonio]-propanesulfonic acid (for instance, CHAPS, manufactured by Dojindo Laboratories), and 3-[(3-cholamido propyl)dimethylammonio]-2-hydroxypropanesulfonic acid (for instance, CHAPSO, manufactured by Dojindo Laboratories). The amount to be used is usually 0.01–2 wt. %.

The surfactant is usually mixed in a buffer solution, but it is not limited. In some cases, the surfactant is mixed with an enzyme solution, or with an enzyme reaction solution individually as a surfactant solution. However, the surfactant can not be mixed with a substrate solution. When the surfactant coexists with a substrate by mixing with a substrate solution before the preparation of an enzyme reaction solution, the protease activity does not improve.

For example, when UTI is measured, the measuring method of the present invention is carried out as follows.

First, a urine sample, a buffer solution and an enzyme solution are mixed. The ratio (volume ratio) is usually set in the range of urine sample: buffer solution: enzyme solution= 1:5–20:2–10. This is incubated generally at 25–37° C. for 1–5 minutes. The substrate solution is then mixed therein, thus reacting the enzyme generally at 25–37° C. for 1–20 minutes. The mixing ratio is usually in the range of 5–30 vol. % in the entire reaction solution. In this case, the pH of the reaction solution varies depending on the kind of the enzyme or the like. However, the pH of the trypsin as an example is preferably 7–8. Then, the enzyme activity is detected by the predetermined method, thus measuring the enzyme activity. In this reaction, the enzyme reaction is inhibited corresponding to the amount of UTI in the urine sample. Therefore, when a calibration curve has been prepared by using known amount of UTI, the UTI amount can be determined by measuring the enzyme activity. In a method of detecting the enzyme activity, for example, when using a substrate such as BAPNA or the like that exhibits colors by the enzyme reaction, the level of the colors is measured by using a spectrophotometer or the like. Besides the method described above, the enzyme activity can be determined by measuring the concentration of the reaction product.

The measuring kits of the present invention include a kit comprising, for example, the buffer solution R1, the enzyme solution R2, and the substrate solution R3. These reagents (R1, R2 and R3) can be prepared by the method described above in the description of the measuring method of the present invention. Each composition, ratio and the like are the same as those mentioned in the description of the measuring method. By using this measuring kit, the concentration or the activity of protease inhibitor such as UTI or the like can be measured easily and quickly.

Examples will be explained as follows.

EXAMPLE 1

We prepared a buffer solution (R1), an enzyme solution (R2), and a substrate solution (R3) according to the method described above. The compositions are described below.

Buffer Solution R1: pH 8.1

| | |
|---|---|
| triethanolamine hydrochloride | 0.5 mol/L |
| $CaCl_2.2H_2O$ | 150 mg/L |

Enzyme Solution R2

| | |
|---|---|
| trypsin (manufactured by Sigma Chemical Co.) | 50 mg/L |
| HCl | 1 mmol/L |

Substrate Solution R3

We prepared the substrate solution R3 by dissolving L-BAPNA (manufactured by Peptide Institute, Inc., hereafter the same) in warm water at about 70° C. at a ratio of 1 g/L.

Operating Method

Using a physiological salt solution (0.85%) as a sample, we compared the reaction time courses of L-BAPNA and D, L-BAPNA. After mixing 20 μl of the sample, 200 μl of the buffer solution (R1), and 100 μl of the enzyme solution (R2) and incubating it at 37° C. for 5 minutes, we added 100 μl of the substrate solution (R3) therein, resulting in the initiation of the reaction. Then, while keeping it warm at 37° C., we measured the change in the absorbance (405 nm) for two minutes by an autoanalyser, thus determining the relative absorbance (ΔO.D.). The graph of FIG. 1 shows the result. We conducted another measurement by the same method and under the same conditions as in the case mentioned above except using D, L-BAPNA (manufactured by Sigma Chemical Co., hereafter the same). The graph of FIG. 1 shows this result, also.

As can be seen from the graph of FIG. 1, when using L-BAPNA, the sensitivity improves compared to that when using D, L-BAPNA.

EXAMPLE 2

As shown below, we measured the concentration of UTI using four kinds of surfactants (TRITON X-405, TRITON X-100, Tween20, and CHAPS). The compositions of reagents (R1, R2 and R3) and the operating method are described below.

Buffer Solution R1:pH 8.1

| triethanolamine hydrochloride | 0.5 mol/L |
|---|---|
| $CaCl_2 \cdot 2H_2O$ | 150 mg/L |
| Surfactant | 0.1, 0.4 wt. % |

In this case, the surfactant concentration (final concentration) in the enzyme reaction solution was half the concentration mentioned above. As a reference (Ref), we also prepared a buffer solution with a surfactant having a concentration of 0 wt. % and tested it.

Enzyme Solution R2:pH 3.0

| trypsin | 50 mg/L |
|---|---|
| HCl | 1 mmol/L |

Substrate Solution R3

We prepared the substrate solution R3 by dissolving L-BAPNA in warm water at about 70° C. at a ratio of 4.0 g/L.

Operating Method

We prepared four physiological salt solutions for UTI (Miraclid, manufactured by Mochida Pharmaceutical Co., Ltd., hereafter the same) with a different concentration of 0 U/ml, 5 U/ml, 10 U/ml, or 20 U/ml as samples respectively. After mixing 20 μl of the sample, 200 μl of the buffer solution (R1) and 100 μl of the enzyme solution (R2) and incubating it at 37° C. for 5 minutes, we added 100 μl of the substrate solution (R3) therein, resulting in the initiation of the reaction. Then, while keeping it warm at 37° C., we measured the change in the absorbance (405 nm) for two minutes by an autoanalyser, thus determining the relative absorbance (ΔO.D.). Each of the four graphs of FIG. 2 shows the result in each surfactant.

Figure 2:
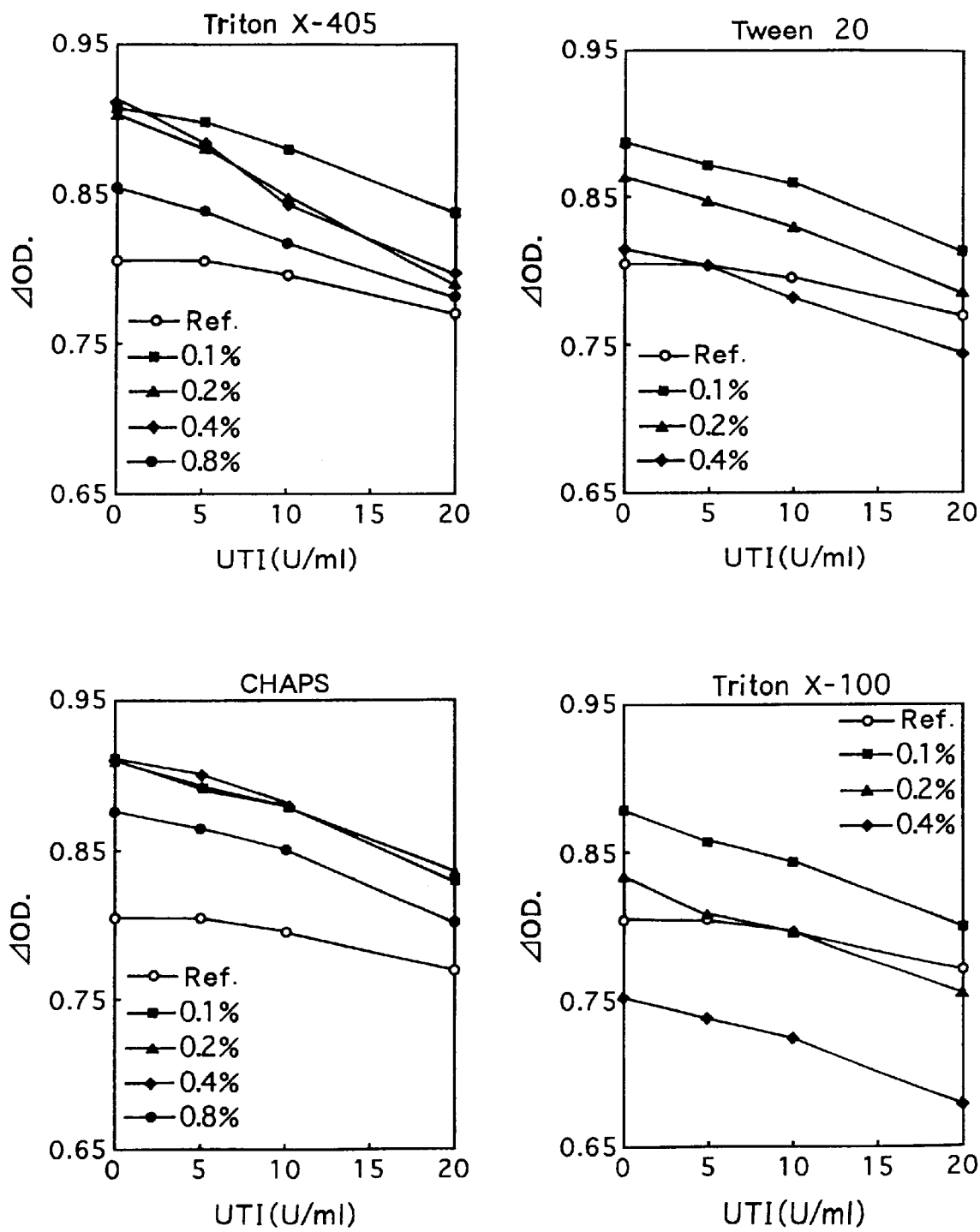
FIG. 2 includes 4 graphs showing the results of the UTI measurement using various surfactants in another example of the measuring method of the present invention.

As can be seen from the four graphs of FIG. 2, the UTI sensitivity improved when using the surfactant mixed in the buffer solution. We confirmed that the UTI sensitivity generally tends to improve, as the surfactant concentration becomes higher.

EXAMPLE 3

As described below, changing the reagent to which the surfactant was added, we measured the concentration of each UTI.

Formula A: The surfactant was added to the buffer solution R1.

Buffer Solution R1:pH 8.1

| triethanolamine hydrochloride | 0.5 mol/L |
|---|---|
| $CaCl_2 \cdot 2H_2O$ | 150 mg/L |
| TRITON X-405 | 2 g/L |

In this case, the surfactant concentration (final concentration) in the enzyme reaction solution was 0.1 wt. % of the concentration mentioned above. This is the same in the following Formulae B and C.

Enzyme Solution R2:pH 3.0

| trypsin | 50 mg/L |
|---|---|
| HCl | 1 mmol/L |

Substrate Solution R3

We prepared the substrate solution R3 by dissolving L-BAPNA in warm water at about 70° C. at a ratio of 4.0 g/L.

Formula B: The surfactant was added to the enzyme solution R2.

Buffer Solution R1:pH 8.1

| triethanolamine hydrochloride | 0.5 mol/L |
|---|---|
| $CaCl_2 \cdot 2H_2O$ | 150 mg/L |

Enzyme Solution R2:pH 3.0

| trypsin | 50 mg/L |
|---|---|
| HCl | 1 mmol/L |
| TRITON X-405 | 4 g/L |

Substrate Solution R3

We prepared the substrate solution R3 by dissolving L-BAPNA in arm water at about 70° C. at a ratio of 4.0 g/L.

Formula C: The surfactant was added to the substrate solution R3.

Buffer Solution R1:pH 8.1

| triethanolamine hydrochloride | 0.5 mol/L |
|---|---|
| $CaCl_2 \cdot 2H_2O$ | 150 mg/L |

Enzyme Solution R2:pH 3.0

| trypsin | 50 mg/L |
|---|---|
| HCl | 1 mmol/L |

Substrate Solution R3

We prepared the substrate solution R3 by dissolving L-BAPNA (4.0 g/L) and TRITON X-405 (4 g/L) in warm water at about 70° C.

Formula D: No surfactant was added.

Buffer Solution R1:pH 8.1

| triethanolamine hydrochloride | 0.5 mol/L |
|---|---|
| $CaCl_2.2H_2O$ | 150 mg/L |

Enzyme Solution R2:pH 3.0

| trypsin | 50 mg/L |
|---|---|
| HCl | 1 mmol/L |

Substrate Solution R3

We prepared the substrate solution R3 by dissolving L-BAPNA (4.0 g/L) in warm water at about 70° C.

Operating Method

We prepared four physiological salt solutions for UTI with a different concentration of 0 U/ml, 5 U/ml, 10 U/ml, or 20 U/ml as samples respectively. After mixing 20 μl of the sample, 200 μl of the buffer solution (R1), and 100 μl of the enzyme solution (R2) and incubating it at 37° C. for 5 minutes, we added 100 μl of the substrate solution (R3) therein, resulting in the initiation of the reaction. Then, while keeping it warm at 37° C., we measured the change in the absorbance (405 nm) for two minutes by an autoanalyser, thus determining the relative absorbance (ΔO.D.). The graph of FIG. 3 shows the result.

Figure 3:
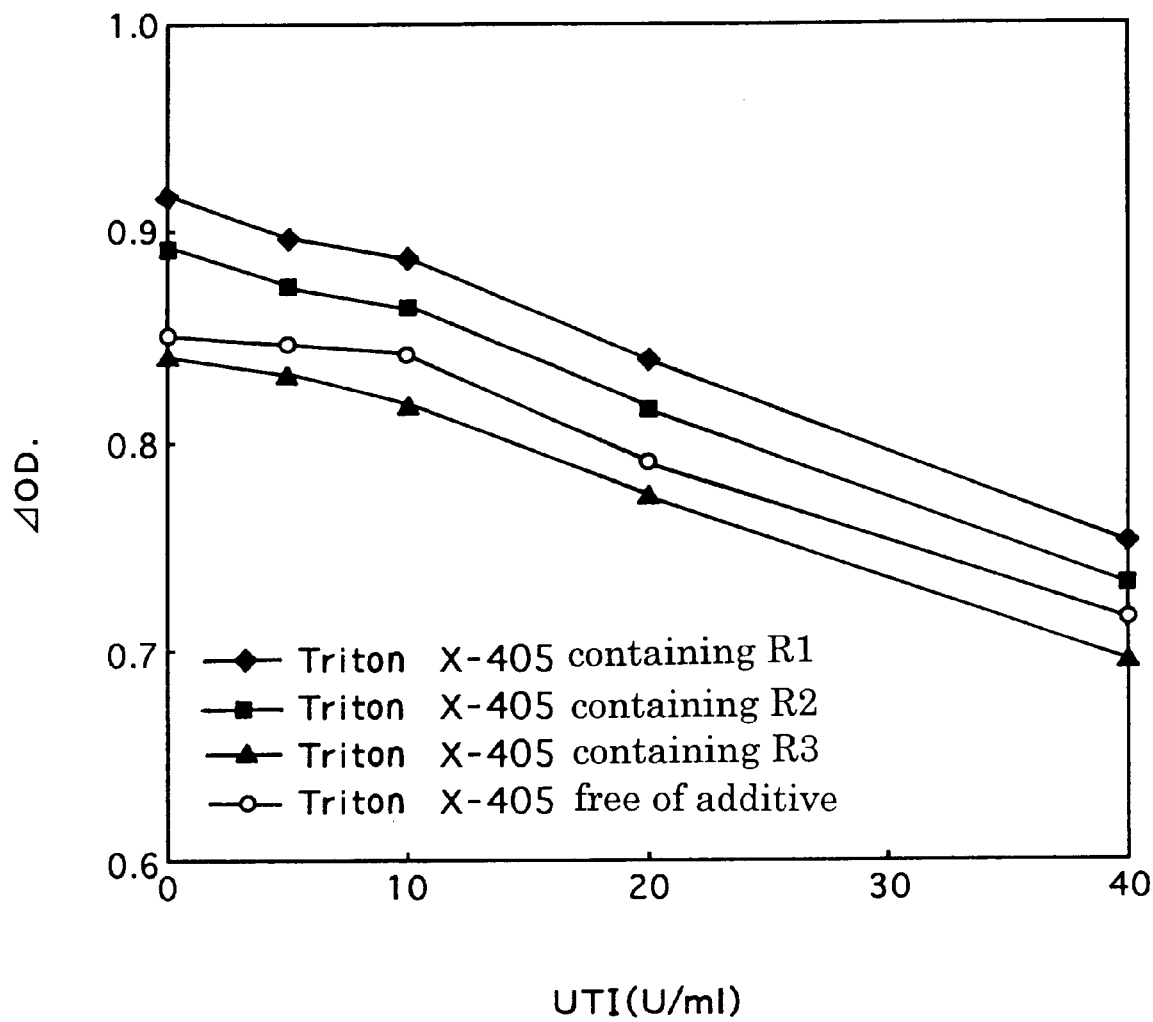
FIG. 3 is a graph showing the results of the UTI measurement with another reagent into which a surfactant is added in further another example of the measuring method of the present invention.

As can be seen from the graph of FIG. 3, the UTI sensitivity improved when employing Formulae A or B in which the surfactant was added to the buffer solution R1 and the enzyme solution R2 respectively compared to the case of employing Formula D in which no surfactant was added. However, in Formula C in which the surfactant was added to the substrate solution R3, the UTI sensitivity deteriorated compared to that in the case of Formula D. Consequently, when the surfactant does not coexist with substrate before preparing the enzyme reaction solution, the UTI sensitivity is improved by adding a surfactant.

EXAMPLE 4

As described below, changing the composition of the substrate solution R3, we measured the concentration of each UTI. The compositions of the buffer solution R1 and the enzyme solution R2 also are described below.

Buffer Solution R1:pH 8.1

| triethanolamine hydrochloride | 0.5 mol/L |
|---|---|
| $CaCl_2.2H_2O$ | 150 mg/L |

Enzyme Solution R2:pH 3.0

| trypsin | 50 mg/L |
|---|---|
| HCl | 1 mmol/L |

Substrate Solution R3

Formula (0)

We prepared the substrate solution R3 by dissolving L-BAPNA (1.0 g/L) in warm water at about 70° C.

Formula (1)

We prepared the substrate solution R3 by dissolving D, L-BAPNA into DMSO and diluting it with a surfactant (CHAPSO) solution. The final concentrations of D, L-BAPNA, DMSO and CHAPSO in the solution were 4 g/L, 10 wt. %, and 1 wt. %, respectively.

Formula (2)

We prepared the substrate solution R3 by the same method as in Formula (1) except using L-BAPNA instead of D, L-BAPNA.

Formula (3)

We prepared the substrate solution R3 by the same method as in Formula (0) except using L-BAPNA (4 g/L) instead of D, L-BAPNA.

Formula (4)

We prepared the substrate solution R3 by dissolving L-BAPNA (4.0 g/L) in warm water at about 70° C. In this Formula (4), we added CHAPSO to the buffer solution R1 at a ratio of 0.5 wt. %.

Operating Method

We prepared six physiological salt solutions for UTI with a different concentration of 0 U/ml, 6.25 U/ml, 12.5 U/ml, 25 U/ml, 50 U/mil, or 100 U/ml as samples respectively. After mixing 20 μl of the sample, 200 μl of the buffer solution (R1), and 100 μl of the enzyme solution (R2) and incubating it at 37° C. for 5 minutes, we added 100 μl of the substrate solution (R3) therein, resulting in the initiation of the reaction. Then, while keeping it warm at 37° C., we measured the change in the absorbance (405 nm) for two minutes by an autoanalyser, thus determining the relative absorbance (ΔO.D.). The graphs of FIG. 4 show the results.

In FIG. 4, Graph A shows all results of five Formulae (0, 1, 2, 3, and 4), and Graph B shows the results of Formulae (1) and (4). As can be seen from the graphs, the UTI sensitivity in Formulae (3) and (4) according to the present invention was higher than that in the conventional three Formulae (0, 1, and 2). Especially, in Formula (4) in which the surfactant was added to the buffer solution R1, the UTI sensitivity was extremely high.

As described above, according to the method for measuring the concentration or the activity of protease inhibitor of the present invention, the higher substrate concentration than that in the method using an organic solvent such as DMSO or the like can be obtained and the sensitivity also improves. Therefore, by applying the measuring method of the present invention, the concentration or the activity of protease inhibitor can be measured quickly and easily at high sensitivity. Consequently, for example, the present invention makes it possible to take full advantage of UTI as a useful indicator of infectious disease or the like in the field of clinical medicine or the like. Furthermore, as described above, since an organic solvent is not used in the measuring method of the present invention, the preparation process of a substrate solution can be simplified. In addition, damage in plastic cell is not caused, and the material costs can be reduced. Consequently, the measuring method of the present invention can be easily applied to the examination using an autoanalyser or the like with low costs.

The invention may be embodied in other forms without departing from the spirit or essential characteristics thereof The embodiments disclosed in this application are to be considered in all respects as illustrative and not restrictive, the scope of the invention is indicated by the appended claims rather than by the foregoing description, and all changes which come within the meaning and range of equivalency of the claims are intended to be embraced therein.

What is claimed is:

1. A method for measuring a concentration or an activity of urinary trypsin inhibitor (UTI) in a sample, comprising:

providing the sample, a protease comprising trypsin or chymotrypsin, a synthetic substrate and a surfactant, with the surfactant being provided separately from the synthetic substrate;

mixing the sample, the protease comprising trypsin or chymotrypsin, the synthetic substrate and the surfactant to form a reaction solution, wherein the surfactant is maintained separate from the substrate before being mixed in the reaction solution;

measuring a protease activity; and determining the concentration of UTI based on the protease activity.

2. A method for measuring a concentration or an activity of urinary trypsin inhibitor (UTI) in a sample, comprising:

providing the sample, a protease comprising trypsin or chymotrypsin, a synthetic substrate and a surfactant, with the surfactant being provided separately from the synthetic substrate;

mixing the sample, the protease comprising trypsin or chymotrypsin, the synthetic substrate and the surfactant to form a reaction solution, wherein the surfactant is maintained separate from the substrate before being mixed in the reaction solution;

measuring a protease activity; and determining the concentration of UTI based on the protease activity, wherein the substrate comprises one or more amino acid residue, all of which is of L-type.

3. A measuring method according to claim 1 or 2, wherein the surfactant concentration in the enzyme reaction solution is 0.01–2 wt. %.

4. The measuring method according to claim 1 or 2, wherein the surfactant is at least one selected from the group consisting of polyoxyethylene sorbitan monolaurate, polyoxyethylene sorbitan monooleate, polyoxyethylene sorbitan monostearate, sorbitan monopalmitate, sorbitan monooleate, sorbitan monolaurate, polyoxyethylene (10) octylphenylether, polyoxyethylene (30) octylphenylether, polyoxyethylene (40) octylphenylether, 1-O-n-octyl-β-D-glucopyranoside, sucrose monolaurate, 3-[(3-cholamido propyl)dimethylammonio]-propanesulfonic acid, 3-[(3-cholamido propyl)dimethylammonio]-2-hydroxypropanesulfonic acid, cetyltrimethylammonium bromide, and benzyltrimethylammonium hydroxide.

5. The measuring method of any one of claims 1 or 2, wherein trypsin, the sample is urine, and the protease activity is measured in the presence of calcium.

6. The measuring method according to any one of claims 1 or 2, wherein the synthetic substrate is dissolved in a liquid consisting essentially of an aqueous medium.

7. The measuring method according to claim 2, wherein the substrate is expressed by the formula:

Protecting Groups-(L-type Amino Acid Residues)$_n$-p-Nitroanilide, wherein n is an integer of 1–5.

8. The measuring method according to claim 7, wherein the substrate is α-benzoyl-L-arginine-p-nitroanilide.

* * * * *